US012692210B2

(12) United States Patent
Ali Almajnouni et al.

(10) Patent No.:  US 12,692,210 B2
(45) Date of Patent:  Jul. 28, 2026

(54) METHODS AND APPARATUSES FOR PROCESSING HYDROCARBONS TO PRODUCE LIGHT OLEFINS

(71) Applicants:Saudi Arabian Oil Company, Dhahran (SA); King Abdullah University of Science and Technology, Thuwal (SA)

(72) Inventors: Khalid Ali Almajnouni, Dhahran (SA); Ola S. Ali, Dhahran (SA); Jorge Gascon Sabate, Thuwal (SA); Isa Al Aslani, Thuwal (SA); Shatha Ali Alabbad, Dhahran (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 882 days.

(21) Appl. No.: 18/063,154

(22) Filed: Dec. 8, 2022

(65) Prior Publication Data

US 2024/0190793 A1     Jun. 13, 2024

(51) Int. Cl.
C10G 11/00      (2006.01)
C07C 4/06      (2006.01)
C10G 11/05      (2006.01)

(52) U.S. Cl.
CPC ................ C07C 4/06 (2013.01); C10G 11/05 (2013.01); *C07C 2529/40* (2013.01);
(Continued)

(58) Field of Classification Search
CPC ...................................................... C10G 11/00
See application file for complete search history.

(56) References Cited

U.S. PATENT DOCUMENTS

| | | | |
|---|---|---|---|
| 2,685,498 A | 8/1954 | Dickinson | |
| 2,929,774 A | 3/1960 | Smith | |

(Continued)

FOREIGN PATENT DOCUMENTS

| | | |
|---|---|---|
| EP | 2301658 A1 | 3/2011 |
| WO | 2018169768 A1 | 9/2018 |

OTHER PUBLICATIONS

International Report on Patentability for corresponding PCT Application No. PCT/US2023/082865 dated Feb. 19, 2025 (10 pages).

(Continued)

*Primary Examiner* — Randy Boyer
(74) *Attorney, Agent, or Firm* — Leason Ellis LLP

(57)          ABSTRACT

Light olefins may be produced from hydrocarbons by a method including passing a hydrocarbon feed stream into one or more feed inlets of a reactor, with one or more co-feeds of steam, a recycle stream or oxygenates. The reactor may include an upper reactor portion defining an upper reaction zone and a lower reactor portion defining a lower reaction zone. The catalyst may move in a generally downward direction through the upper reactor portion and the lower reactor portion, and the hydrocarbon feed stream may move in a generally upward direction through the lower reactor portion and upper reactor portion such that the hydrocarbon feed stream and the catalyst move with a counter-current orientation. Contacting the catalyst with the hydrocarbon feed stream may crack one or more components of the hydrocarbon feed stream and form a hydrocarbon product stream.

11 Claims, 4 Drawing Sheets

(52) U.S. Cl.

CPC ................ *C10G 2300/1033* (2013.01); *C10G 2300/1044* (2013.01); *C10G 2300/1048* (2013.01); *C10G 2300/1051* (2013.01); *C10G 2300/1088* (2013.01); *C10G 2300/1096* (2013.01); *C10G 2400/20* (2013.01)

(56) References Cited

U.S. PATENT DOCUMENTS

| | | | |
|---|---|---|---|
| 3,082,165 | A | 3/1963 | Hugo et al. |
| 3,650,946 | A | 3/1972 | Mourning |
| 3,799,868 | A | 3/1974 | Gantt |
| 3,837,822 | A * | 9/1974 | Ward .................... B01J 8/125 |
| | | | 48/197 R |
| 3,879,281 | A | 4/1975 | Jones |
| 4,259,175 | A | 3/1981 | McArthur |
| 4,356,082 | A | 10/1982 | Gross |
| 4,427,537 | A * | 1/1984 | Dean .................... C10G 11/18 |
| | | | 422/140 |
| 4,820,493 | A | 4/1989 | Haddad et al. |
| 4,869,807 | A | 9/1989 | Krishna |
| 5,062,944 | A | 11/1991 | Leib et al. |
| 5,451,313 | A | 9/1995 | Wegerer et al. |
| 5,468,369 | A | 11/1995 | Muldowney |
| 5,616,237 | A | 4/1997 | Krishna et al. |
| 6,656,346 | B2 | 12/2003 | Ino et al. |
| 7,077,949 | B2 | 7/2006 | Bakker et al. |
| 7,594,994 | B1 | 9/2009 | Seibert et al. |
| 8,349,170 | B2 | 1/2013 | Tammera et al. |
| 9,388,095 | B2 | 7/2016 | Leroy et al. |
| 9,452,404 | B2 | 9/2016 | Marri et al. |
| 9,458,394 | B2 | 10/2016 | Dean et al. |
| 11,446,625 | B2 | 9/2022 | Gascon et al. |
| 2004/0024276 | A1 | 2/2004 | Smith et al. |
| 2004/0104148 | A1 | 6/2004 | Lomas et al. |
| 2006/0108261 | A1 * | 5/2006 | Steffens .................... C07C 4/06 |
| | | | 585/653 |
| 2008/0035526 | A1 | 2/2008 | Hedrick et al. |
| 2009/0187059 | A1 | 7/2009 | Chewter et al. |
| 2013/0178672 | A1 | 7/2013 | Chen et al. |
| 2013/0338418 | A1 | 12/2013 | Xu et al. |
| 2014/0014555 | A1 * | 1/2014 | Marri .................... B01J 8/0015 |
| | | | 208/78 |
| 2016/0160134 | A1 | 6/2016 | Voolapalli et al. |
| 2017/0087528 | A1 | 3/2017 | Pretz et al. |
| 2021/0317373 | A1 | 10/2021 | Gong et al. |
| 2022/0033714 | A1 | 2/2022 | Al-Majnouni et al. |

OTHER PUBLICATIONS

Alabdullah et al. "Composition-performance Relationships in Catalysts Formulation for the Direct Conversion of Crude Oil to Chemicals." ChemCatChem 13.7 (2021): 1806-1813.

Alabdullah et al. "One-step conversion of crude oil to light olefins using a multi-zone reactor." Nature Catalysis 4.3 (2021): 233-241.

Jakobsen. "Chapter 6: Chemical Reaction Engineering." Chemical Reactor Modeling. 2nd Edition, 2014. Springer, Cham. https://doi.org/10.1007/978-3-319-05092-8_6. pp. 789-790.

Jakobsen. "Chapter 10: Fluidized Bed Reactors." Chemical Reactor Modeling. 2nd Edition, 2014. Springer, Cham. https://doi.org/10.1007/978-3-319-05092-8_10. pp. 1005-1017.

International Search Report and Written Opinion in corresponding PCT Application No. PCT/US2023/082865, dated May 7, 2024; 21 pages.

Written Opinion of the International Searching Authority in corresponding PCT Application No. PCT/US2023/082865, mailed Oct. 24, 2024; 9 pages.

Letter with Demand in corresponding PCT Application No. PCT/US2023/082865, filed Sep. 24, 2024; 4 pages.

* cited by examiner

1

METHODS AND APPARATUSES FOR PROCESSING HYDROCARBONS TO PRODUCE LIGHT OLEFINS

TECHNICAL FIELD

Embodiments of the present disclosure generally relate to methods for processing hydrocarbons, and more specifically, to methods for processing hydrocarbons to produce olefins.

DESCRIPTION OF RELATED ART

Light olefins, including ethylene, propylene, and butene, are basic intermediates used by a large portion of the petrochemical industry. In particular, pure streams of light olefins may be used during the production of various polymers and chemicals. Traditionally, light olefins may be produced by thermal cracking of petroleum fractions such as naphtha, kerosene, or gas oil. Light olefins could also be produced by fluid catalytic cracking (FCC) processes. As the demand for light olefins increases, there is a need for improved methods to produce light olefins.

It is in regard to these and other problems in the art that the present disclosure is directed to provide a technical solution for improved methods to produce light olefins.

SUMMARY OF THE DISCLOSURE

Methods for processing hydrocarbons to produce light olefins are provided. Light olefins may be produced from hydrocarbons by a method including passing a hydrocarbon feed stream into one or more feed inlets of a reactor, with one or more co-feeds of steam, a recycle stream or oxygenates. The reactor may include an upper reactor portion defining an upper reaction zone and a lower reactor portion defining a lower reaction zone. The catalyst may move in a generally downward direction through the upper reactor portion and the lower reactor portion, and the hydrocarbon feed stream may move in a generally upward direction through the lower reactor portion and upper reactor portion such that the hydrocarbon feed stream and the catalyst move with a counter-current orientation. Contacting the catalyst with the hydrocarbon feed stream may crack one or more components of the hydrocarbon feed stream and form a hydrocarbon product stream. The method may further include passing the hydrocarbon product stream out of the upper reaction zone through the hydrocarbon product outlet.

In certain embodiments, a method for processing hydrocarbons to produce light olefins comprises passing a primary hydrocarbon feed stream, and a co-feed of steam, to a feed inlet of a reactor for contact with catalyst, the co-feed provided in an amount of about 1 to 150 mass percent of the co-feed relative to a mass of the primary hydrocarbon feed stream.

In certain embodiments, a method for processing hydrocarbons to produce light olefins comprises passing a primary hydrocarbon feed stream, and a co-feed of a recycle stream derived from a hydrocarbon product stream.

In certain embodiments, a method for processing hydrocarbons to produce light olefins comprises passing a primary hydrocarbon feed stream, and a co-feed of oxygenates, a feed inlet of a reactor for contact with a catalyst, the co-feed provided in an amount of about 1 to 50 mass percent of the co-feed relative to a mass of the primary hydrocarbon feed stream.

In certain embodiments, a method for processing hydrocarbons to produce light olefins comprises passing a primary hydrocarbon feed stream and co-feeds to a feed inlet of a reactor for contact with catalyst, the co-feed comprising steam in an amount of about 1 to 150 mass percent of the steam relative to a mass of the primary hydrocarbon feed stream, and recycle oil derived from a hydrocarbon product stream.

In certain embodiments, a method for processing hydrocarbons to produce light olefins comprises passing a primary hydrocarbon feed stream and co-feeds to a feed inlet of a reactor for contact with catalyst, the co-feed comprising steam in an amount of about 1 to 150 mass percent of the steam relative to a mass of the primary hydrocarbon feed stream, and oxygenates in an amount of about 1 to 50 mass percent relative to a mass of the primary hydrocarbon feed stream.

In certain embodiments, a method for processing hydrocarbons to produce light olefins comprises passing a primary hydrocarbon feed stream and co-feeds to a feed inlet of a reactor for contact with catalyst, the co-feed comprising steam in an amount of about 1 to 150 mass percent of the steam relative to a mass of the primary hydrocarbon feed stream, recycle oil derived from a hydrocarbon product stream, and oxygenates in an amount of about 1 to 50 mass percent relative to a mass of the primary hydrocarbon feed stream.

In certain embodiments, a method for processing hydrocarbons to produce light olefins comprises passing a first hydrocarbon feed stream into a first feed inlet of a reactor and a second hydrocarbon feed stream into a second feed inlet of the reactor, for contact with catalyst.

In certain embodiments in which a recycle oil stream comprises all or part of a co-feed, other reaction products comprise at least light cycle oil, and wherein the co-feed comprises as all or a portion of the recycle stream all or a portion of the light cycle oil, and wherein the recycle stream is provided in an amount of about 1 to 20 mas percent of the co-feed relative to the primary hydrocarbon feed stream. In certain embodiments in which a recycle oil stream comprises all or part of a co-feed, other reaction products comprise at least light naphtha, and wherein the co-feed comprises as all or a portion of the recycle stream all or a portion of the light naphtha, and wherein the recycle stream is provided in an amount of about 1 to 50 mass percent of the co-feed relative to the primary hydrocarbon feed stream.

In certain embodiments in which oxygenates comprise all or a part of the co-feed, oxygenates may comprise one or more alcohols, ketones or aldehydes. In certain embodiments in which oxygenates comprise all or a part of the co-feed, methanol may be used.

In the herein embodiments, the reactor comprises: an upper reactor portion defining an upper reaction zone, the upper reactor portion comprising a catalyst inlet for receiving the catalyst and a hydrocarbon product outlet, wherein the catalyst inlet and the hydrocarbon product outlet are positioned at or near the top of the upper reaction zone, and wherein a reaction zone refers to an area where a particular reaction takes place in the reactor; and a lower reactor portion defining a lower reaction zone, the lower reactor portion comprising the feed inlet and a catalyst outlet, wherein the feed inlet and the catalyst outlet are positioned at or near the bottom of the lower reaction zone, and wherein the lower reaction zone is in fluid communication with and adjacent to the upper reaction zone. The catalyst has a downward superficial velocity through the upper reaction zone and the lower reaction zone and the hydrocarbon feed stream has an upward superficial velocity through the upper reaction zone and lower reaction zone such that the hydrocarbon feed stream and the catalyst move with a counter-current orientation and contact. The upper reaction zone operates with a counter-current plug flow regime, wherein a catalyst-to-oil ratio on a mass basis in the upper reaction zone is from about 5 to 100 and the superficial velocity of the hydrocarbon feed stream in the upper reaction zone is 10 m/s or less. The lower reaction zone operates with a dense bed fluidization regime, wherein a weight hourly space velocity of the lower reaction zone is from about 1 to 200 $hr^{-1}$. Contacting the catalyst with the hydrocarbon feed stream and the co-feed cracks one or more components of the hydrocarbon feed stream and forms the hydrocarbon product stream. The hydrocarbon product stream comprises light olefins including one or more of ethylene, propylene, or butene, and can also include other reaction products including light cycle oil and one or more of dry gas, LPG, aromatics, light naphtha, full range naphtha, heavy naphtha, or heavy cycle oil. The hydrocarbon product stream is passed out of the upper reaction zone through the hydrocarbon product outlet.

In certain embodiments, the methods further comprise; passing the catalyst through the catalyst outlet to a catalyst regenerator, wherein the catalyst passing through the catalyst outlet is spent catalyst; regenerating at least a portion of the spent catalyst to form a regenerated catalyst; and passing the regenerated catalyst to the upper reaction zone through the catalyst inlet. The method can also comprise passing the catalyst through a steam stripping portion of the reactor prior to the catalyst outlet. For example, in the steam stripping portion, steam contacts the catalyst and at least a portion of hydrocarbons adsorbed on the catalyst are stripped from the catalyst.

Any combinations of the various embodiments and implementations disclosed herein can be used. These and other aspects and features can be appreciated from the following description of certain embodiments and the accompanying drawings and claims.

BRIEF DESCRIPTION OF DRAWINGS

The following detailed description of specific embodiments of the present disclosure can be best understood when read in conjunction with the following drawings, where like structure is indicated with like reference numerals.

DETAILED DESCRIPTION

Figure 1:
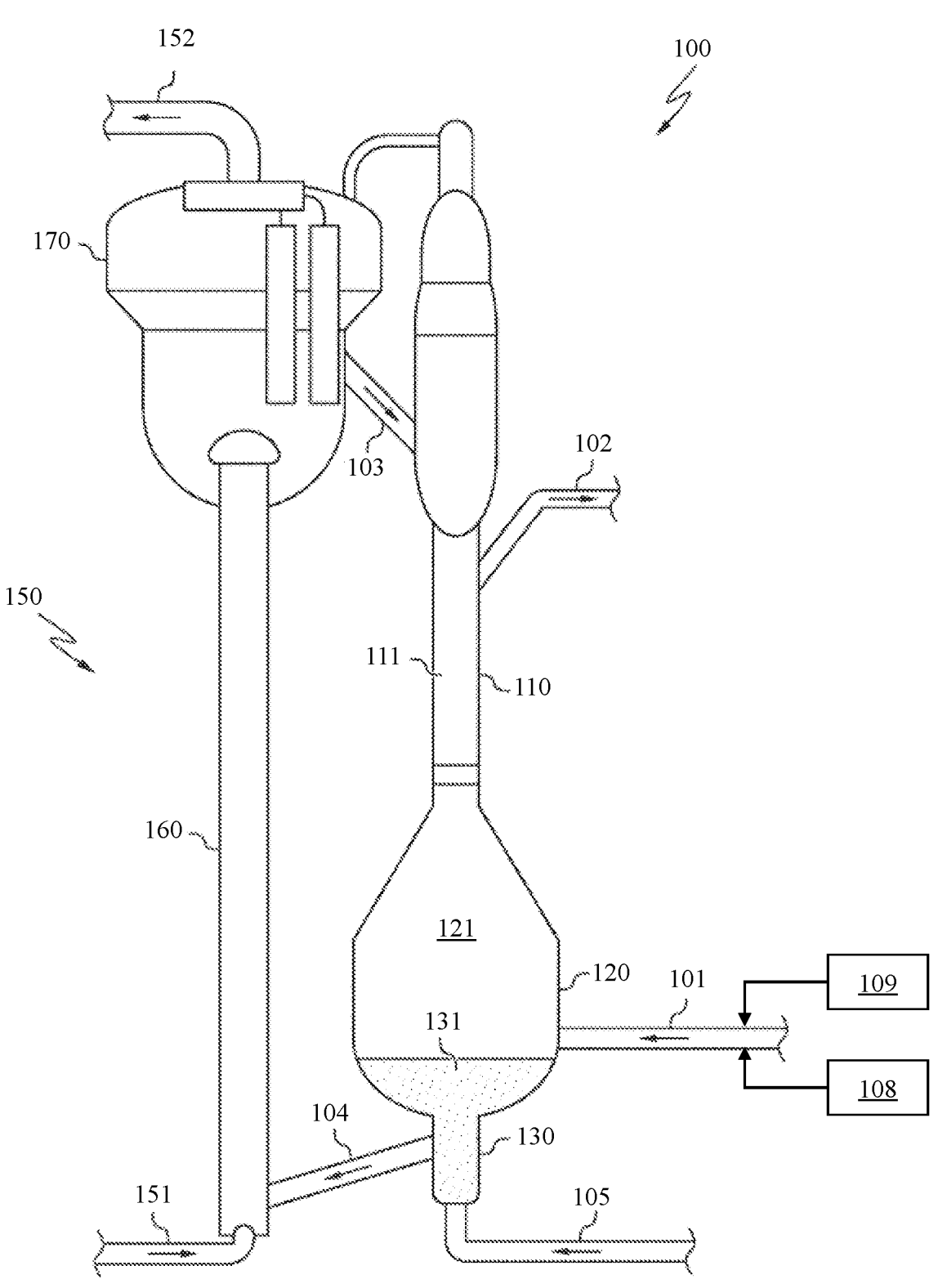
FIG. 1 schematically depicts a reactor and catalyst regenerator for producing light olefins according to one or more embodiments disclosed herein.

Embodiments of the present disclosure are directed to systems and processes for processing hydrocarbons to produce light olefins. The present disclosure includes embodiments related to the methods and apparatuses described in commonly owned U.S. patent application Ser. No. 16/940, 668 filed Jul. 28, 2020, entitled "Methods and apparatuses for processing hydrocarbons to produce light olefins" and published as US20220033714A1, which is incorporated by reference herein in its entirety.

As used in this disclosure, a "reactor" refers to a vessel in which one or more chemical reactions may occur between one or more reactants in the presence of one or more catalysts. One or more "reaction zones" may be disposed in a reactor. As used in this disclosure, a "reaction zone" refers to an area where a particular reaction takes place in a reactor. In certain embodiments, a reaction zone comprises an area that is arranged as a counter-current plug flow reactor. In certain embodiments, a reactor comprises a reaction zone comprises an area that is arranged as a dense bed fluidized reactor. In certain embodiments, a reactor comprises one reaction zone that is an area arranged as a counter-current plug flow reactor, and another reaction zone that is a separate area is arranged as a dense bed fluidized reactor. In certain embodiments, a reactor comprises a stripping zone to strip hydrocarbons adsorbed on the catalyst.

As used in this disclosure, "hydrocarbon reactants" refer to hydrocarbons from a hydrocarbon feed stream that are passing through the reactor, and may include one or more initial hydrocarbon feed streams, one or more recycle streams, and one or more co-feeds containing hydrocarbons. In certain embodiments "hydrocarbon reactants" refer to hydrocarbons from a primary or initial hydrocarbon feed stream that are passing through the reactor, and may include one or more co-feeds, including steam and/or oxygenates. In certain embodiments "hydrocarbon reactants" refer to hydrocarbons from a primary hydrocarbon feed stream that are passing through the reactor, and may include one or more recycle feeds, such as at least a portion of cycle oil (light, heavy or a combined cycle oil stream) from reactor effluents. In certain embodiments "hydrocarbon reactants" refer to hydrocarbons from a primary hydrocarbon feed stream that are passing through the reactor, and may include one or more recycle feeds, such as at least a portion of light cycle oil from reactor effluents, and one or more co-feeds, including steam and/or oxygenates. In certain embodiments "hydrocarbon reactants" refer to hydrocarbons from a first hydrocarbon feed stream fed via a first feed inlet of the reactor and a second hydrocarbon feed stream fed via a second feed inlet of the reactor, which are passing through the reactor. In certain embodiments "hydrocarbon reactants" refer to hydrocarbons from a first hydrocarbon feed stream fed via a first feed inlet of the reactor and a second hydrocarbon feed stream fed via a second feed inlet of the reactor, which are passing through the reactor, and one or more co-feeds, including steam and/or oxygenates, which are passed together with the first and/or second hydrocarbon feed streams. In certain embodiments "hydrocarbon reactants" refer to hydrocarbons from a first hydrocarbon feed stream fed via a first feed inlet of the reactor and a second hydrocarbon feed stream fed via a second feed inlet of the reactor, which are passing through the reactor, and one or more recycle feeds, such as at least a portion of cycle oil (light cycle oil, heavy cycle oil or a combination thereof) from reactor effluents, which are passed together with the first and/or second hydrocarbon feed streams. In certain embodiments "hydrocarbon reactants" refer to hydrocarbons from a first hydrocarbon feed stream fed via a first feed inlet of the reactor and a second hydrocarbon feed stream fed via a second feed inlet of the reactor, which are passing through the reactor, and one or more recycle feeds, such as at least a portion of light cycle oil from reactor effluents, and one or more co-feeds, including steam and/or oxygenates, wherein the recycle and co-feeds are passed together with the first and/or second hydrocarbon feed streams.

As used in this disclosure, a "catalyst" refers to any substance which increases the rate of a specific chemical reaction. Catalysts described in this disclosure may be utilized to promote various reactions, such as, but not limited to, cracking. As used in this disclosure, "cracking" generally refers to a chemical reaction where a molecule having carbon to carbon bonds is broken into more than one molecule by the breaking of one or more of the carbon to carbon bonds, or is converted from a compound which includes a cyclic moiety, such as a cycloalkane, cycloalkene, naphthalene or the like, to a compound which does not include a cyclic moiety or contains fewer cyclic moieties than prior to cracking.

As used in this disclosure, the term "spent catalyst" refers to catalyst that has been introduced to and passed through a reaction zone to crack a hydrocarbon feed, but has not been regenerated in the regenerator following introduction to the reaction zone. The "spent catalyst" may have: coke deposited on the catalyst and may include partially coked catalyst as well as fully coked catalysts; and hydrocarbons from the feed or reaction products adsorbed or otherwise deposited on the catalysts. The amount of coke deposited and hydrocarbons adsorbed on the "spent catalyst" may be greater than the amount of coke and hydrocarbons remaining on the regenerated catalyst following regeneration. As used in this disclosure, the "spent catalyst" may have adsorbed hydrocarbons removed in a steam stripping zone in fluid communication with a reaction zone, and spent catalyst containing coke is subjected to regeneration.

As used in this disclosure, the term "regenerated catalyst" refers to catalyst that has been introduced to a reaction zone and then regenerated in a regenerator to heat the catalyst to a greater temperature, oxidize and remove at least a portion of the coke from the catalyst to restore at least a portion of the catalytic activity of the catalyst, or both. The "regenerated catalyst" may have less coke, a greater temperature, or both compared to spent catalyst and may have greater catalytic activity compared to spent catalyst. The "regenerated catalyst" may have more coke and lesser catalytic activity compared to fresh catalyst that has not passed through a cracking reaction zone and regenerator.

As used in this disclosure, the term "stream" (and variations of this term, such as hydrocarbon stream, hydrocarbon feed stream, feedstream, product stream, and the like), unless otherwise specified, may include one or more of various hydrocarbon compounds, such as straight chain, branched or cyclical alkanes, alkenes, alkadienes, alkynes, alkylaromatics, alkenyl aromatics, condensed and non-condensed di-, tri- and tetra-aromatics, and gases such as hydrogen and methane, $C_2+$ hydrocarbons and further may include various impurities. The term "$C_\#$ hydrocarbons" or "$C_\#$", is used herein having its well-known meaning, that is, wherein "#" is an integer value, and means hydrocarbons having that value of carbon atoms. The term "$C_\#+$ hydrocarbons" or "$C_\#+$" refers to hydrocarbons having that value or more carbon atoms. The term "$C_\#-$ hydrocarbons" or "$C_\#-$" refers to hydrocarbons having that value or less carbon atoms. Similarly, ranges are also set forth, for instance, $C_1-C_3$ means a mixture comprising $C_1$, $C_2$ and $C_3$.

The term "crude oil" as used herein refers to a naturally occurring mixture of petroleum liquids and gasses, which can be extracted from geologic formations and can be provided in its unrefined form. Crude oil suitable as the source material for the processes herein include Arabian Heavy, Arabian Light, Arabian Extra Light, other Gulf crudes, Brent, North Sea crudes, North and West African crudes, Indonesian, Chinese crudes, North or South American crudes, Russian and Central Asian crudes, or mixtures thereof. The crude petroleum mixtures can be whole range crude oil or topped crude oil. As used herein, "crude oil" also refers to such mixtures that have undergone some pretreatment such as water-oil separation; and/or gas-oil separation; and/or desalting; and/or stabilization. In certain embodiments, crude oil refers to any of such mixtures having an API gravity (ASTM D287 standard), of greater than or equal to about 25°, 30°, 32°, 34°, 36°, 38°, 40°, 42° or 44°, including those having an API gravity of from 25° to 40°, such as from 25° to 30°, from 30° to 35°, from 35° to 40°, or any combination of these ranges.

As used in this disclosure, all boiling point ranges relative to hydrocarbon fractions derived from crude oil via atmospheric and/or vacuum distillation shall refer to True Boiling Point values obtained from a crude oil assay, or a commercially acceptable equivalent. The modifying term "straight run" is used herein having its well-known meaning, that is, describing fractions derived directly from the atmospheric distillation unit, optionally subjected to steam stripping, without other refinery treatment such as hydroprocessing, fluid catalytic cracking or steam cracking.

As used in this disclosure the acronym "LPG" as used herein refers to the well-known acronym for the term "liquefied petroleum gas," and generally is a mixture of $C_3-C_4$ hydrocarbons. In certain embodiments, these are also referred to as "light ends." The term "naphtha" as used herein refers to hydrocarbons having a nominal boiling range of about 20-210, 20-205, 20-190, 20-180, 20-170, 25-210, 25-205, 25-190, 25-180, 25-170, 32-210, 32-205, 32-190, 32-180, 32-170, 35-210, 35-205, 35-190, 35-180 or 35-170° C. The term "light naphtha" as used herein refers to hydrocarbons having a nominal boiling range of about 20-110, 20-100, 20-90, 20-85, 25-110, 25-100, 25-90, 25-85, 32-110, 32-100, 32-90, 32-85, 35-110, 35-100, 35-90 or 35-85° C. The term "heavy naphtha" as used herein refers to hydrocarbons having a nominal boiling range of about 85-210, 85-205, 85-190, 85-180, 85-170, 90-210, 90-205, 90-190, 90-180, 90-170, 95-210, 95-205, 95-190, 95-180, 95-170, 100-210, 100-205, 100-193, 100-190, 100-180, 100-170, 110-210, 110-205, 110-193, 110-190, 110-180 or 110-170° C. In certain embodiments naphtha, light naphtha and/or heavy naphtha refer to such petroleum fractions obtained by crude oil distillation, or distillation of intermediate refinery processes. The term "kerosene" as used herein refers to hydrocarbons having a nominal boiling range of about 160-280, 160-270, 160-260, 170-280, 170-270, 170-260, 180-280, 180-270, 180-260, 190-280, 190-270, 190-260, 193-280, 193-270 or 193-260° C. In certain embodiments, the term "middle distillate" is used with reference to one or more fractions containing hydrocarbons having a nominal boiling range of about 160-400, 160-380, 160-370, 160-360, 160-340, 170-400, 170-380, 170-370, 170-360, 170-340, 180-400, 180-380, 180-370, 180-360, 180-340, 190-400, 190-380, 190-370, 190-360, 190-340, 193-400, 193-380, 193-370, 193-360, or 193-340° C. In certain embodiments, the term "straight run middle distillate" is used with reference to one or more straight run fractions from the atmospheric distillation unit. In embodiments in which other terminology is used herein, the middle distillate fraction can also include all or a portion of atmospheric gas oil range hydrocarbons and/or all or a portion of kerosene. In additional embodiments, term "middle distillate" is used to refer to fractions from one or more operations boiling in this range. The term "atmospheric residue" as used herein refer to the bottom hydrocarbons having an initial boiling point corresponding to the end point of the AGO range hydrocarbons, and having an end point based on the characteristics of the crude oil feed. The term "vacuum gas oil" as used herein refer to hydrocarbons having a nominal boiling range of about 370-565, 370-550, 370-540, 370-530, 370-510, 400-565, 400-550, 400-540, 400-530, 400-510, 420-565, 420-550, 420-540, 420-530 or 420-510° C. The term "vacuum residue" as used herein refer to the bottom hydrocarbons having an initial boiling point corresponding to the end point of the vacuum gas oil range hydrocarbons, and having an end point based on the characteristics of the crude oil feed.

The term "condensates" refers to hydrocarbons separated from natural gas stream. As used herein, "condensates" also refers to such mixtures that have undergone some pretreatment such as water-oil separation; and/or gas-oil separation; and/or desalting; and/or stabilization. In certain embodiments, condensates refer to any of such mixtures having an API gravity (ASTM D287 standard), of greater than or equal to about 45, 50, 60, or 65°.

The term "cycle oil" is used herein to refer to a mixture of light cycle oil and heavy cycle oil. The term "light cycle oil" and its acronym "LCO" as used herein refers to the light cycle oil produced by conventional FCC units, and is also used to refer to corresponding ranges of hydrocarbons from the countercurrent multizone fluidized bed reactor herein. The nominal boiling range for LCO is, for example, in the range of about 215-350, 216-350, 220-350, 215-343, 216-343, 220-343, 215-330, 216-330 or 220-330° C. The term "heavy cycle oil" and its acronym "HCO" as used herein refer to the heavy cycle oil which is produced by conventional FCC units, and is also used to refer to corresponding ranges of hydrocarbons from the countercurrent multizone fluidized bed reactor. The nominal boiling range for HCO is, for example, in the range of about 330+, 343+ or 350+, for instance 330-530, 330-510, 343-530, 343-510, 350-530 or 350-510° C.

Conventional FCC processes operate with a relatively low catalyst hold up in the reactor by utilizing lean bed or circulating fluidization regimes, such as dilute fluidized beds. Additionally, conventional catalytic cracking processes may utilize co-current flow patterns whereby the catalyst and hydrocarbons flow through the reactor in the same direction, which can result in undesirable flow patterns such as back-mixing and core-annular flow. Embodiments of the present disclosure are directed to methods to produce light olefins by catalytic cracking, where the catalyst and hydrocarbons contact each other in a counter-current manner and where a portion of the reactor operates with a dense bed fluidization regime. Dense bed fluidization may allow more catalyst to be present in the reactor, which in turn may lead to higher conversion of the hydrocarbon and higher yield of light olefins than observed in traditional catalytic cracking processes. Counter-current flow may be describable to increase the conversion of the feed. For example, during counter-current flow, fresh catalyst may move from the top of the reactor to the bottom of the reactor while hydrocarbon feed flows from the bottom to the top of the reactor. The spent catalyst at the bottom of the reactor and nearing the exit of the reactor contacts with the feed flowing upward and converts the reactive components in the feed including the heavy fraction of the feed). The less reactive components in the feed are converted as the feed travels upward, contacting the hot and fresh catalyst in the top section of the reactor. Additionally, counter-current contact between the hydrocarbons and catalyst may prevent back-mixing or core-annular flow, which are often leads to a reduced yield of light olefins in traditional FCC riser reactors where the catalyst and hydrocarbons flow through the reactor co-currently.

Figure 2:
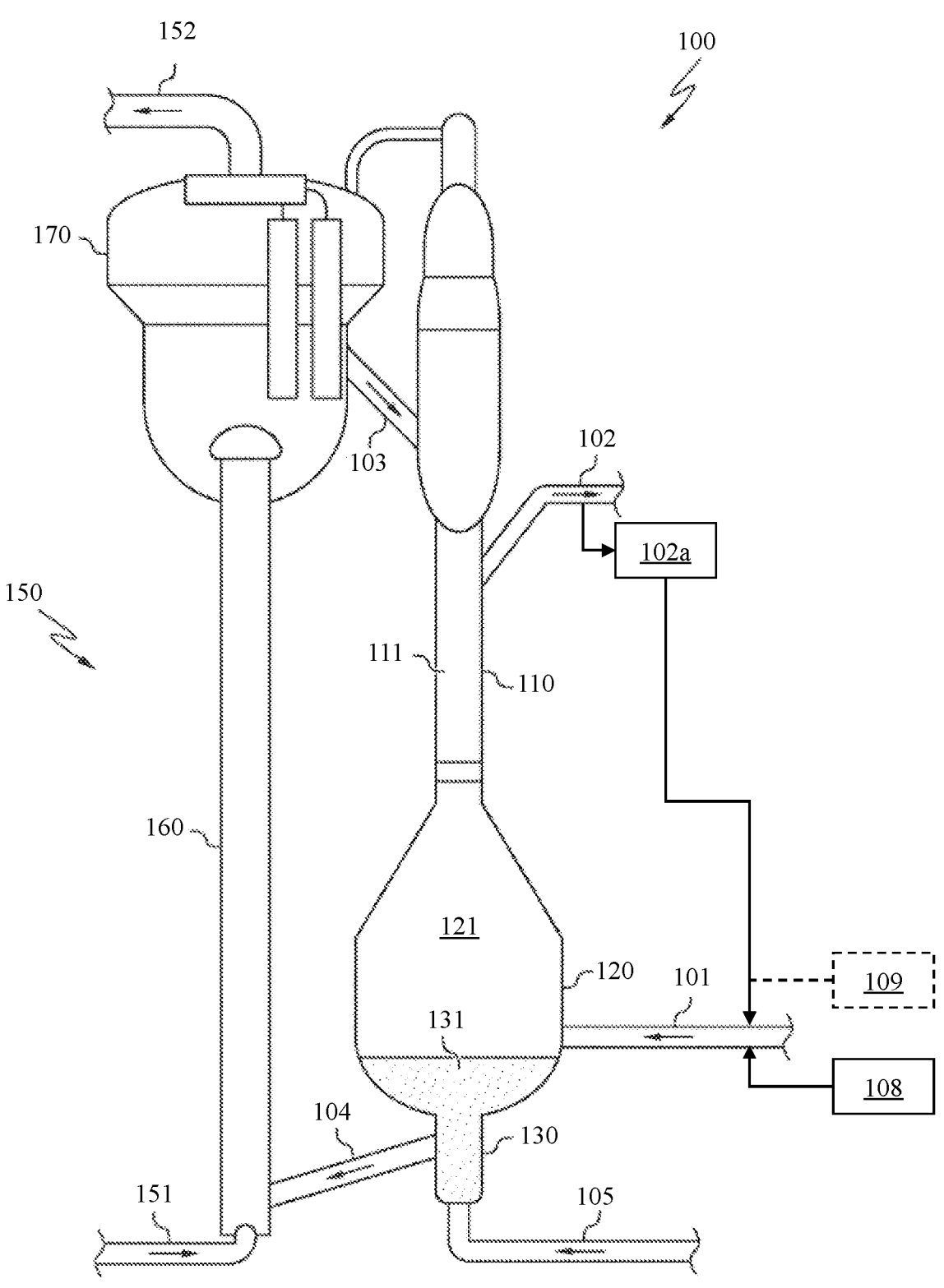
FIG. 2 schematically depicts a reactor and catalyst regenerator for producing light olefins according to one or more further embodiments.

Referring now to FIGS. 1 and 2, a reactor 100 for producing light olefins is schematically depicted. The reactor comprises an upper reactor portion 110, a lower reactor portion 120, and a steam stripping portion 130. The upper reactor portion 110 defines an upper reaction zone 111 and the lower reactor portion 120 defines a lower reaction zone 121. In certain embodiments, operation of reactor 100 includes a primary hydrocarbon feed stream 108 which enters the lower reaction zone 121 through one or more feed inlets 101 located in the lower reactor portion 120. The one or more feed inlets may be positioned at or near the bottom of the lower reactor portion 120. Additionally, the lower reactor portion 120 may comprise one or more catalyst outlets for discharging a stream 104 of spent catalyst, positioned at or near the bottom of the lower reactor portion 120. As described herein, at or near the bottom of the lower reactor portion 120 corresponds to positions in the bottom 10%, bottom 5%, or bottom 1% of the height of the lower reactor portion 120.

In certain embodiments, as shown with respect to FIG. 1, a co-feed 109 is introduced with the primary hydrocarbon feed stream 108 through one or more feed inlets 101 located in the lower reactor portion 120. In certain embodiments, a co-feed 109 is fed to the reactor via the same feed inlet 101 as the hydrocarbon feed stream 108.

In certain embodiments, as shown with respect to FIG. 2, a recycle stream 102a is introduced with the primary hydrocarbon feed stream 108 through one or more feed inlets 101 located in the lower reactor portion 120. In certain embodiments, a recycle stream 102a is fed to the reactor via the same feed inlet 101 as the hydrocarbon feed stream 108. In addition, optional embodiments as shown in FIG. 2 also include a co-feed 109 (shown in dashed lines) that is introduced with the primary hydrocarbon feed stream 108 and the recycle stream 102a through one or more feed inlets 101.

Figure 3:
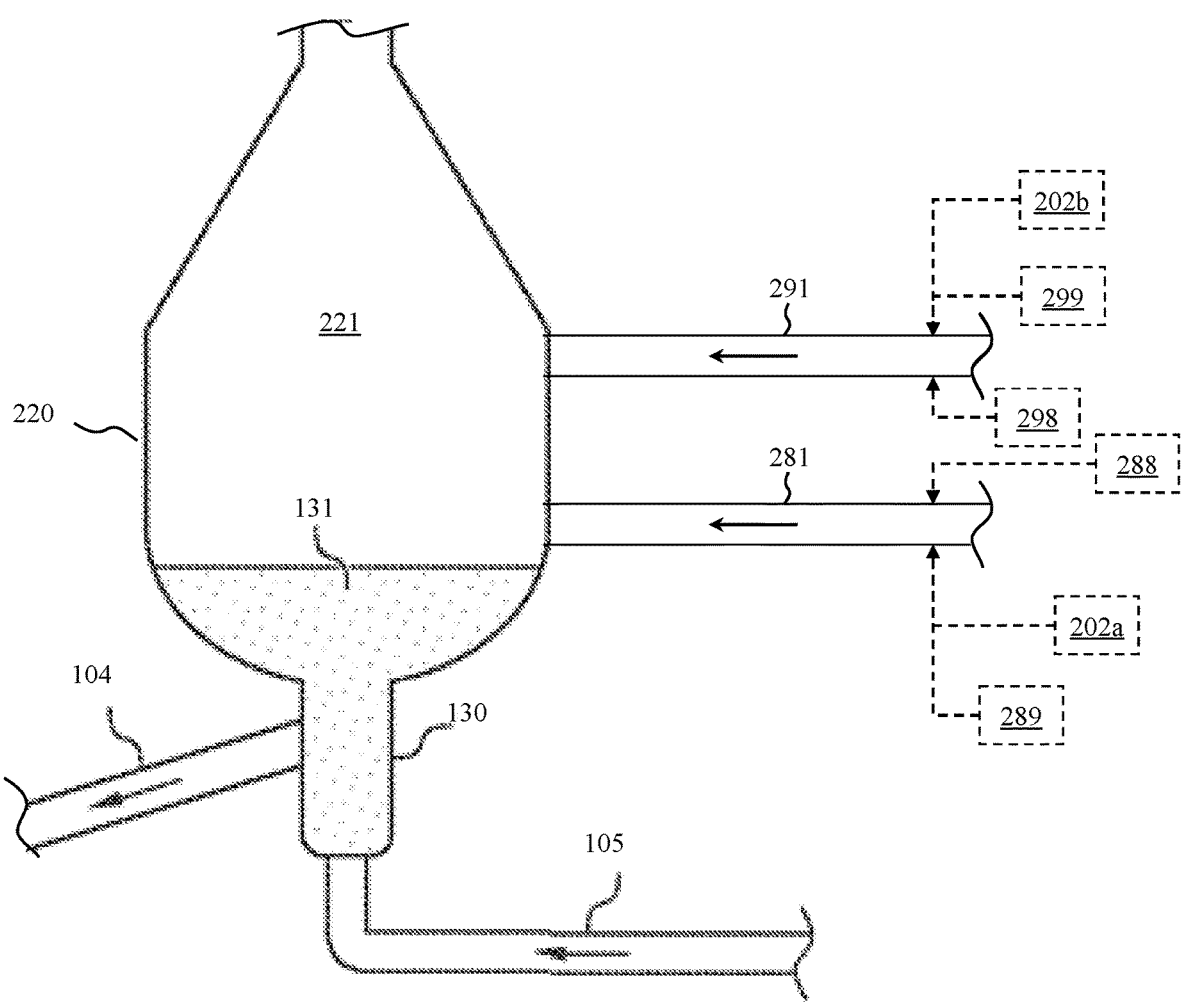
FIG. 3 schematically the lower reactor portion of a reactor for producing light olefins according to one or more additional embodiments disclosed herein.

In certain embodiments, as shown with respect to FIG. 3, another embodiment of a lower reactor portion, lower reactor portion 220, is provided, that can be used with other components of the reactor 100 of FIGS. 1 and 2, or with the reactor described in US20220033714A1. The lower reactor portion 220 defines a lower reaction zone 221, and includes one or more first inlets 281 and one or more second inlets 291. The one or more first feed inlets 281 may be positioned at or near the bottom of the lower reactor portion 220. The one or more second feed inlets 291 may be positioned mid-height of the lower reactor portion 220 or positioned at or near the top of the lower reactor portion 220. In certain embodiments, one inlet is provided as a first feed inlet 281, and one inlet is provided as a second feed inlet 291. As described herein, at or near the bottom of the lower reactor portion 220 corresponds to positions in the bottom 10%, bottom 5%, or bottom 1% of the height of the lower reactor portion 220. As described herein, at or near the top of the lower reactor portion 220 corresponds to positions in the top 10%, top 5%, or top 1% of the height of the lower reactor portion 220. As described herein, positioned mid-height of the lower reactor portion 220 to positions from the bottom 15%, bottom 25%, or bottom 35% of the height of the lower reactor portion 220 spanning to positions from the top 15%, top 25%, or top 35% of the height of the lower reactor portion 220, for example, an inlet positioned mid-height of the lower reactor portion 220 may be in a location between the bottom 15% to the top 15%, the bottom 25% to the top 25% or the bottom 35% to the top 35%.

A feed to the one or more first inlets 281 include one or more of: a first hydrocarbon feed stream 288, a recycle stream 202*a*, or a co-feed 289 (or plural co-feeds 289). In certain embodiments a feed to the one or more first inlets 281 include a first hydrocarbon feed stream 288. In certain embodiments the feed to the one or more first inlets 281 include the first hydrocarbon feed stream 288 and the co-feed 289 (or plural co-feeds 289). In certain embodiments the feeds to the one or more first inlets 281 include the first hydrocarbon feed stream 288 and the recycle stream 202*a*. In certain embodiments the feed to the one or more first inlets 281 include a first hydrocarbon feed stream 288, a recycle stream 202*a*, and a co-feed 289 (or plural co-feeds 289). In certain embodiments the feed to the one or more first inlets 281 include the recycle stream 202*a*. In certain embodiments the feed to the one or more first inlets 281 include the recycle stream 202*a* and a co-feed 289 (or plural co-feeds 289).

A feed to the one or more second inlets 291 include one or more of: a second hydrocarbon feed stream 298, a recycle stream 202*b*, or a co-feed 299 (or plural co-feeds 299) In certain embodiments a feed to the one or more second inlets 291 include a second hydrocarbon feed stream 298. In certain embodiments the feed to the one or more second inlets 291 include the second hydrocarbon feed stream 298 and the co-feed 299 (or plural co-feeds 299). In certain embodiments the feed to the one or more second inlets 291 include the second hydrocarbon feed stream 298 and the recycle stream 202*b*. In certain embodiments the feed to the one or more second inlets 291 include a second hydrocarbon feed stream 298, a recycle stream 202*b*, and a co-feed 299 (or plural co-feeds 299). In certain embodiments the feed to the one or more second inlets 291 include the recycle stream 202*b*. In certain embodiments the feed to the one or more second inlets 291 include a recycle stream 202*b* and a co-feed 299 (or plural co-feeds 299).

With continued reference to FIGS. 1 and 2, and also to FIG. 3, the upper reactor portion 110 defines an upper reaction zone 111. In operation the hydrocarbon reactants move through the lower reaction zone 121 or 221 and into the upper reaction zone 111. The upper reactor portion 110 and the lower reactor portion 120 or 220 are in fluid communication with each other. In one or more embodiments, the upper reactor portion 110 and the lower reactor portion 120 or 220 may be adjacent to each other, with no intervening components or reactor portions, whereby the upper reactor portion 110 and the lower reactor portion 120 or 220 are in direct fluid communication with each other. In one or more embodiments, the hydrocarbon reactants pass directly from the lower reactor portion 120 or 220 to the upper reactor portion 110.

Figure 4:
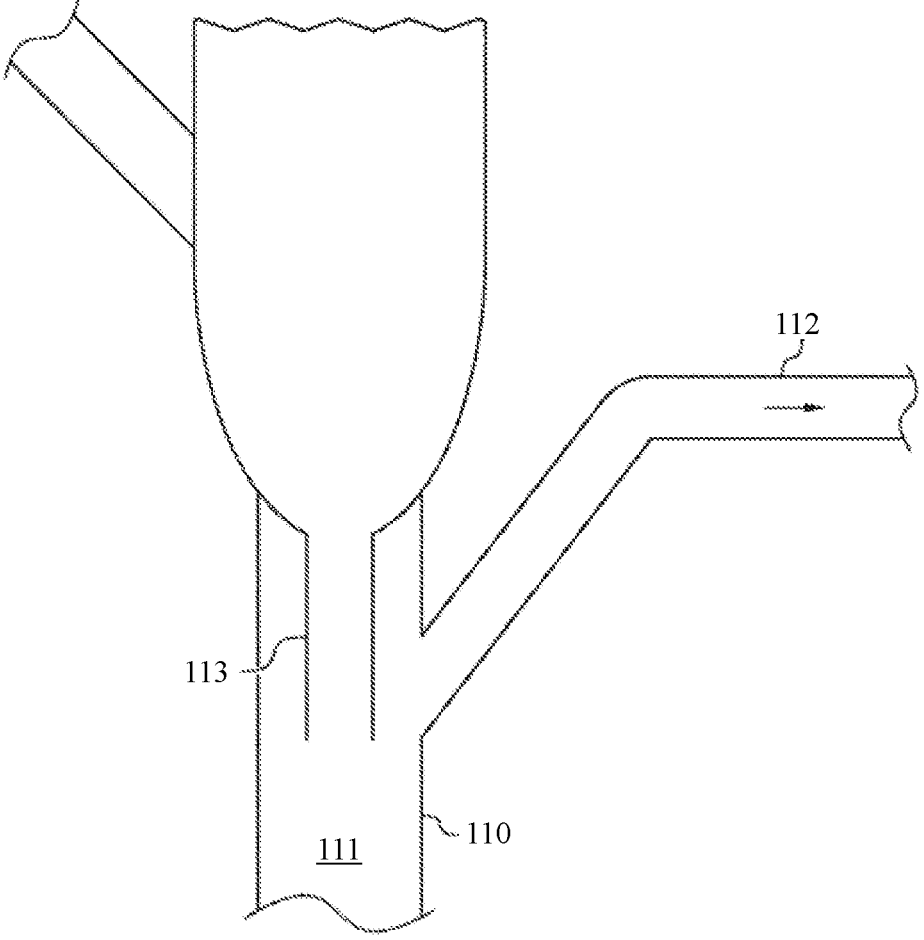
FIG. 4 schematically depicts a cross-sectional view of the upper reactor portion of a reactor for producing light olefins according to one or more embodiments disclosed herein.

Referring to FIG. 4, a cross-sectional view of the upper reactor portion 110 is shown. The upper reactor portion 110 includes a reactor effluent outlet 112 and a catalyst inlet 113, which are positioned at or near the top of the upper reactor portion 110. As described herein, at or near the top of the upper reactor portion 110 corresponds to positions in the top 10%, top 5%, or top 1% of the height of the upper reactor portion 110. Catalyst may enter the upper reactor portion 110 through catalyst inlet 113. As shown in FIG. 4, the catalyst inlet 113 may extend into the upper reactor portion 110 so the catalyst enters the upper reaction zone 111 below the hydrocarbon product outlet 112. Also as shown in FIG. 4, the hydrocarbon product outlet 112 is defined by an opening in the upper reactor portion 110, and the hydrocarbon product outlet 112 does not extend into upper reaction zone 111. Thus, catalyst may enter the upper reaction zone below the hydrocarbon outlet 112. Without wishing to be bound by theory, it is believed that introducing the catalyst below the hydrocarbon product outlet 112 may reduce the amount of catalyst entrained in the hydrocarbon product exiting the reactor 100.

As shown in FIGS. 1-3, the lower reactor portion 120 or 220 may have a larger cross-sectional area than the upper reactor portion 110. In certain embodiments, the lower portion 120 or 220 and the lower reaction zone 121 or 221 is characterized by a shape that is a cylindrical portion. In one or more embodiments, the lower reactor portion 120 or 220 may have a substantially similar cross-sectional area to the upper reactor portion 110. In certain embodiments, the lower portion 120 or 220 and the lower reaction zone 121 or 221 is characterized by a shape that is a cylindrical portion surmounted with a frustoconical portion. In either embodiment, when referring to the position of the one or more first feed inlets 281 and the one or more second feed inlets 291, the percentages of height as related to the bottom height, mid-height and the top height refer to the height along the cylindrical portion of the lower reactor portion 220.

In one or more embodiments, the upper reaction zone 111 may operate in a counter-current plug flow regime. In one or more embodiments, the hydrocarbon reactants may exhibit plug flow as they move up through the upper reaction zone 111. Likewise, the catalyst may exhibit plug flow as it moves down through the upper reaction zone 111. Since the flow of catalyst is opposed to the flow of the hydrocarbon feed, the flows are counter-current and the upper reaction zone 111 may operate in a counter-current plug flow regime.

In one or more embodiments, the catalyst-to-oil ratio in the upper reaction zone 111 may be from about 5-100. For example, the catalyst-to-oil ratio in the upper reaction zone 111 may be from about 5-100, 10-100, 20-100, 30-100, 40-100, 50-100, 60-100, 70-100, 80-100, 90-100, 5-90, 5-80, 5-70, 5-60, 5-50, 5-40, 5030, 5-20 or 5-10. Without wishing to be bound by theory, it is believed that there is less constraint on catalyst-to-oil ratios suitable for use in the upper reaction zone 111 because the catalyst may flow through the upper reaction zone 111 by gravity instead of being transported through the reactor by the flow of hydrocarbons. Additionally, a high catalyst-to-oil ratio indicates a large amount of catalyst within the upper reaction zone 111, which is believed to lead to increased conversion of the hydrocarbon feed to light olefins.

The catalyst may move through the upper reaction zone 111 and into the lower reaction zone 121 or 221. In one or more embodiments, the catalyst may pass directly from the upper reaction zone 111 to the lower reaction zone 121 or 221. The lower reaction zone 121 or 221 may operate in a dense bed fluidization regime. In one or more embodiments, the catalyst may pass from the upper reaction zone 111 to the lower reaction zone 121 or 221 and form a dense fluidized bed in the lower reaction zone 121 or 221. As described herein, a "dense bed fluidization regime" refers to fluidization regimes in which the fluidized bed has a clearly defined upper limit or surface to the dense bed. For example, dense bed fluidization regimes include the smooth fluidization, bubbling fluidization, slugging fluidization, and turbulent fluidization regimes. In a dense fluidized bed, the particle entrainment rate may be low, but may increase as the velocity of the gas flowing through the bed increases.

In one or more embodiments, the initial hydrocarbon feed stream 108, or the first hydrocarbon feed stream 288 and/or the second hydrocarbon feed stream 298, may comprise, consist of, or consist essentially of crude oil. In further embodiments, the initial hydrocarbon feed stream 108, or the first hydrocarbon feed stream 288 and/or the second hydrocarbon feed stream 298, may comprise, consist of, or consist essentially of a fraction of crude oil, or a petrochemical product formed from a crude oil, having an initial boiling point of at least 25° C. For example, in one or more embodiments, the initial hydrocarbon feed stream 108, or the first hydrocarbon feed stream 298 and/or the second hydrocarbon feed stream 298, may comprise, consist of, or consist essentially of light naphtha and may have an initial boiling point from about 20° C. to about 35° C. and a final boiling point of from about 85° C. to about 110° C. In one or more embodiments, the initial hydrocarbon feed stream 108, or the first hydrocarbon feed stream 288 and/or the second hydrocarbon feed stream 298, may comprise, consist of, or consist essentially of heavy naphtha and may have an initial boiling point from about 85° C. to about 110° C. and a final boiling point from about 170° C. to about 210° C. In further embodiments, the initial hydrocarbon feed stream 108, or the first hydrocarbon feed stream 288 and/or the second hydrocarbon feed stream 298, may comprise, consist of, or consist essentially of full range naphtha and have an initial boiling point from about 20° C. to about 35° C. and a final boiling point from about 170° C. to about 210° C.

In one or more embodiments, the initial hydrocarbon feed stream 108, or the first hydrocarbon feed stream 288 and/or the second hydrocarbon feed stream 298, may comprise, consist of, or consist essentially of one or more of $C_4$ components, light naphtha, heavy naphtha, full range naphtha, vacuum gas oil, crude oil, FCC gasoline, olefinic naphtha, atmospheric residue, vacuum residue, condensate, deasphalted crude oil, dewaxed crude oil, deasphalted-dewaxed crude oil, middle distillates, or kerosene.

In one or more embodiments, a co-feed 109 as in the embodiment of FIG. 1, an optional co-feed 109 as in the embodiment of FIG. 2, an optional co-feed 209 as in the embodiment of FIG. 3, and/or an optional co-feed 289 as in the embodiment of FIG. 3, comprises steam. In embodiment in which steam is provided as a co-feed, it is provided in an amount of about 1 to 150 mass percent of the co-feed relative to a mass of the initial hydrocarbon feed, for example, in an amount of about 1 wt. %, 5 wt. %. 10 wt. %, 20 wt. %, 30 wt. %, 40 wt. %, 50 wt. %, 60 wt. %, 70 wt. %, 80 wt. %, 90 wt. %, 100 wt. %, 110 wt. %, 120 wt. %, 130 wt. %, 140 wt. % or any amount between about 1 to 150, 10 to 150, 20 to 150, 10 to 100, 10 to 70 or 10 to 40 wt. %.

In one or more embodiments, a co-feed 109 as in the embodiment of FIG. 1, an optional co-feed 109 as in the embodiment of FIG. 2, an optional co-feed 209 as in the embodiment of FIG. 3, and/or an optional co-feed 289 as in the embodiment of FIG. 3, comprises one or more oxygenates. In embodiment in which oxygenates are provided as a co-feed, it is provided in an amount of about 1 to 50 wt. % by mass relative to the mass of the initial hydrocarbon feed, for example, of about 1 wt. %, 5 wt. %, 10 wt. %, 15 wt. %, 20 wt. %, 25 wt. %, 30 wt. %, 35 wt. %, 40 wt. %, 45 wt. %, 50 wt. % or any amount between about 1 to 50 wt. %. In one or more embodiments, oxygenates may comprise one or more alcohols, ketones or aldehydes. In one or more embodiments, an oxygenate may comprise methanol.

In one or more embodiments, a recycle stream 102a, or a recycle stream 202a and/or a recycle stream 202b, comprise at least a portion of other reaction products derived from the hydrocarbon product stream 102. In one or more embodiments, the hydrocarbon product stream 102 is fractioned into one or more fractions of light naphtha, non-aromatic naphtha, medium naphtha, heavy naphtha, light cycle oil, heavy cycle oil, or heavy oil, a fraction rich in olefinic butenes, and any one or more of said fractions comprise the recycle stream 102a, or 202a and/or 202b. In certain embodiments, the recycle stream 102a, or 202a and/or 202b, comprises, consists of or consists essentially of light cycle oil. In certain embodiments, the recycle stream 102a, or 202a and/or 202b, is provided in an amount of about 1 to 20 wt. % by mass relative to the mass of the initial hydrocarbon feed, for example, about 1 wt. %, 2 wt. %, 5 wt. %, 10 wt. %, 15 wt. %, 20 wt. % or any amount between about 1 to 20, 5 to 20 or 10 to 20 wt. %.

In certain embodiments, the recycle stream 102a, or 202a and/or 202b, comprises non-aromatic light naphtha including butenes (with some of butane and isobutane). In certain embodiments, the recycle stream 102a, or 202a and/or 202b, is provided in an amount of about 1 to 50 wt. % by mass relative to the mass of the initial hydrocarbon feed, for example, about 1 wt. %, 2 wt. %, 5 wt. %, 10 wt. %, 15 wt. %, 20 wt. %, 25 wt. %, 30 wt. %, 35 wt. % or any amount between about 1 to 50, 5 to 50, 10 to 50 or 20 to 50 wt. %.

With reference to FIG. 2, the recycle stream 102a is introduced with the feed stream 108 and optionally one or more co-feeds 109. In certain embodiments, the recycle stream 102a is combined with the initial feed stream 108. In certain embodiments, the recycle stream 102a is combined with the initial feed stream 108 and a co-feed 109 (or plural co-feeds). In certain embodiments, the recycle stream 102a is combined with the initial feed stream 108 and a co-feed 109 of steam. In certain embodiments, the recycle stream 102a is combined with the initial feed stream 108 and a co-feed 109 of one or more oxygenates. In certain embodiments, the recycle stream 102a is combined with the initial feed stream 108 and a co-feed 109 of steam and one or more oxygenates.

With reference to FIG. 3, the first inlet 281 and the second inlet 291 may receive the same or different feeds. As described herein, more active catalyst is towards the top of the lower reaction zone (zone 221 in the example of FIG. 3).

In certain embodiments, an initial feed stream is divided by volume or mass, with a first portion passing to the first inlet 281 as the first hydrocarbon feed stream 288, and a second portion passing to the second inlet 291 as the second hydrocarbon feed stream 298.

In certain embodiments, an initial feed stream is fractioned based on nominal boiling point, wherein a first portion having one or more first boiling point range(s) is passed to the first inlet 281 as the first hydrocarbon feed stream 288, and wherein a second portion having one or more second boiling point range(s) is passed to the second inlet 291 as the second hydrocarbon feed stream 298. For example, in some embodiments, an initial stream can be fractioned into a light portion and a heavy portion, whereby the first hydrocarbon feed stream 288 comprises the light portion and the second hydrocarbon feed stream 298 comprises a heavy portion. In certain embodiments, a cut point between a light and heavy portion is in the range of about 200-375° C., for example about 200, 225, 250, 275, 300, 325, 350 or 375. In some embodiments, a light portion may comprise naphtha range hydrocarbons, for example olefinic rich $C_4$-$C_6$ hydrocarbons, and a heavy portion may comprise the initial feed stream such as crude oil or another initial hydrocarbon feed stream, for instance initial hydrocarbon feed stream 108 above.

In one or more embodiments, the catalyst may comprise a zeolite catalyst, for example, USY zeolite, ZSM-5 zeolite, or a combination of multiple types of suitable zeolite catalysts. Alternatively, the catalyst may comprise other suitable solid acid catalysts. In one or more embodiments, the catalyst may comprise fresh catalyst, regenerated catalyst, or combinations of fresh and regenerated catalyst as described in further detail herein. In one or more embodiments, the catalyst may comprise binders, promotors, inert, and matrix to have acceptable physical and chemical properties such as catalyst attrition index and catalyst density so that it can be used in the proposed reactor configuration.

In one or more embodiments, the weight hourly space velocity (WHSV) of the lower reaction zone 121 or 221 may be from about 1-200 hr$^{-1}$. For example, the WHSV of the lower reaction zone 121 or 221 may be from about 1-200, 1-175, 1-150, 1-125, 1-100, 1-75, 1-50, 1-25, 25-200, 50-200, 75-200, 100-200, 125-200, 150-200 or 175-200 hr$^{-1}$. WHSV may be used to describe the amount of catalyst in the dense bed of the lower reaction zone 121 or 221. Without wishing to be bound by theory, it is believed that a dense bed allows a large amount of catalyst to be present in the lower reaction zone, which may increase the yield of light olefins.

As the hydrocarbon reactants and the catalyst move through the reactor 100, the hydrocarbon reactants may have an upward superficial velocity through a horizontal cross-section of the reactor 100, and the catalyst may have a downward superficial velocity through a horizontal cross-section of the reactor 100. As described herein, "superficial velocity" refers to the velocity at which an individual phase flows through a given cross-sectional area. The bulk flow of a phase is used to determine superficial velocity of that phase; thus, individual particles or molecules within a phase may move in a direction different from, or even opposite to, the bulk flow of a phase without affecting the direction of the superficial velocity of that phase.

For example, the hydrocarbon reactants flow from the feed inlet(s) in the lower reactor portion 120 or 220 to the hydrocarbon product outlet 112 in the upper reactor portion 110. Thus, the bulk flow of hydrocarbon reactants moving through a horizontal cross-section of the reactor 100 is in an upward direction, resulting in an upward superficial velocity. Likewise, the catalyst flows from the catalyst inlet 113 to the catalyst outlet in the steam stripping portion 130 of the reactor 100, and the bulk flow of the catalyst moving through a horizontal cross-section of the reactor 100 is in a downward direction, resulting in a downward superficial velocity. In one or more embodiments, the upward superficial velocity of the hydrocarbon reactants and the downward superficial velocity of the catalyst results in a counter-current flow pattern between the hydrocarbon reactants and the catalyst. Thus, in one or more embodiments, the hydrocarbon reactants and catalyst move with a counter-current orientation.

Without wishing to be bound by theory, it is believed that contacting the hydrocarbon reactants and the catalyst in a counter-current manner may prevent back-mixing of catalyst that may occur in in traditional riser reactors and may promote undesired side reactions that negatively affect the production of light olefins. Additionally, it is believed that contacting the hydrocarbon reactants and the catalyst in a counter-current manner may prevent core-annular flow through the reactor where the catalyst has high concentration near the reactor walls and a low concentration toward the center of the reactor where a majority of the hydrocarbon flow occurs. Generally, core-annular flow reduces the amount of contact between the catalyst and the hydrocarbon, and thus, may reduce the conversion of hydrocarbon feed to light olefins.

Without wishing to be bound by theory, it is also believed that counter-current flow may also result in increased yield of olefins by allowing the more reactive chemicals in the hydrocarbon feed to contact less active catalyst, and less active catalyst to contact more reactive chemicals in the hydrocarbon feed. Generally, the catalyst in the lower reaction zone 121 or 221 has already contacted hydrocarbons in the upper reaction zone 111. Thus, the catalyst in the lower reaction zone 121 or 221 is usually partially spent and has a lower activity than the catalyst in the upper reaction zone 111. Contacting the hydrocarbon feed with a large amount of less active catalyst in the lower reaction zone 121 or 221 may allow the more reactive chemicals in the hydrocarbon feed to crack in the lower reaction zone 121 or 221 while contacting the less active catalyst. This in turn allows the more active catalyst in the upper reaction zone 111 to crack the less reactive chemicals in the hydrocarbon feed, increasing the yield of light olefins produced from the hydrocarbon feed.

In one or more embodiments, the superficial velocity of the hydrocarbon feed stream 101 moving through the upper reactor portion 111 is 10 m/s or less. For example, the superficial velocity of the hydrocarbon feed stream through the upper reactor portion 111 may be less than or equal to 10.0, 9.0, 8.0, 7.0, 6.0, 5.0, 4.0, 3.0, 2.0, 1.0, 0.9, 0.8, 0.7, 0.6, 0.5 or 0.4 m/s. Without wishing to be bound by theory, it is believed that a hydrocarbon feed stream superficial velocity below 10.0 m/s within the upper reactor portion 111 may result in increased contact between the catalyst and the hydrocarbons, which may in turn lead to increased conversion of the hydrocarbon feed to light olefins, and reduced mass transfer limitation between the hydrocarbon feed and catalyst. The superficial velocity of the hydrocarbon feed stream 101 may be attained within the desired range based on design parameters of the reactor 100 including the height and diameter of the upper reactor portion 110 and the lower reactor portion 120 or 220.

In one or more embodiments, the residence time of the hydrocarbon feed stream 101 within the reactor 100 is from about 0.1-10 seconds. For example, the residence time of the hydrocarbon feed stream 101 within reactor 100 may be from about 0.1-10, 0.5-10, 1-10, 2-10, 3010, 4-10, 5-10, 6-10, 7-10, 8-10, 9-10, 0.1-9, 0.1-8, 0.1-7, 0.1-6, 0.1-5, 0.1-4, 0.1-3, 0.1-2 or 0.1-1 second(s).

As the hydrocarbon feed stream 101 contacts the catalyst, at least a portion of the hydrocarbon feed stream 101 may be cracked to form a hydrocarbon product. In one or more embodiments, the temperature within the reactor 100 may be from about 420-750° ° C. to facilitate the cracking of hydrocarbon feed stream 101. For example, the temperature (in ° C.) within the reactor 100 may be from about 420-750, 460-750, 500-750, 540-750, 580-750, 620-750, 660-750, 700-750, 420-670, 420-630, 420-590, 420-550, 420-510, 440-720 or 480-680.

In one or more embodiments, the hydrocarbon product may comprise light olefins and other reactions products. For example, the hydrocarbon product may comprise, ethylene, propylene, butene or combinations of these in addition to the other reactions products. In one or more embodiments, the other reaction products may comprise one or more of dry gas, aromatics, LPG, naphtha (including full range naphtha, or separate light and heavy naphtha fractions), light cycle oil, heavy cycle oil, and/or heavy oil. In one or more embodiments, a hydrocarbon product stream 102 comprising light olefins may be passed from the upper reaction zone 111 through hydrocarbon product outlet 112 in the upper reactor portion 110. In one or more embodiments, the hydrocarbon product stream 102 may comprise catalyst entrained within the hydrocarbon product stream 102 which may be separated from the hydrocarbon product stream 102 in a separation device. Any suitable separation device, including a cyclone or series of cyclones, may be used to separate entrained catalyst from the hydrocarbon product stream 102. In one or more embodiments, the light olefins may be separated from the hydrocarbon product stream 102. Separation of the light olefins from the hydrocarbon product stream may be achieved by any suitable means including, for example, distillation. In one or more embodiments, the separation of light olefins from the hydrocarbon product stream may result in relatively pure streams of ethylene, propylene, or butene.

In one or more embodiments, cracking of the hydrocarbon feed stream 101 may produce spent catalyst. Spent catalyst may be produced in both the upper reaction zone 111 and the lower reaction zone 121 or 221. In one or more embodiments, spent catalyst may comprise coke on the catalyst. The coke may reduce the activity of the catalyst, and spent catalyst may have reduced activity when compared to regenerated or fresh catalyst. In one or more embodiments, the dense fluidized bed of the lower reaction zone 121 or 221 may comprise spent catalyst. Without wishing to be bound by theory, the more reactive components of the hydrocarbon feed stream may crack in the lower reaction zone because high catalytic activity is not required for those components to react. As the hydrocarbon feed passes from the lower reaction zone 121 or 221 to the upper reaction zone 111, the hydrocarbon feed will encounter more active, fresh or regenerated catalyst, and the less reactive components of the hydrocarbon feed will crack. Thus, the counter-current flow of the catalyst and the hydrocarbon feed stream 101 may result in increased conversion of hydrocarbon feed to light olefins.

In one or more embodiments, the reactor 100 may comprise a steam stripping portion 130 below the lower reactor portion 120 or 220. The steam stripping portion 130 may define a steam stripping zone 131. The steam stripping portion 130 may be in fluid communication with and adjacent to the lower reactor portion 120 or 220. In one or more embodiments, spent catalyst may pass from the lower reaction zone 121 or 221 to the steam stripping zone 131. In further embodiments, the spent catalyst may pass directly from the lower reaction zone 121 to the steam stripping zone 131, whereby the lower reaction zone 121 or 221, and the steam stripping zone 131, are in direct fluid communication with each other. Steam may be passed to the steam stripping zone 131 by stream 105. In the steam stripping zone 131, steam may contact the spent catalyst and strip at least a portion of hydrocarbons from the spent catalyst. After contacting the steam in the steam stripping zone 131, spent catalyst may be passed in stream 104 from the reactor 100 through the catalyst outlet. In embodiments in which a co-feed is used and comprises steam, that co-feed with the hydrocarbon feed stream is in addition to the steam introduced to the steam stripping zone 131 by stream 105.

In one or more embodiments, the spent catalyst may be passed to a catalyst regenerator 150 where the spent catalyst is regenerated to form a regenerated catalyst. The catalyst regenerator 150 may comprise a riser 160 and a regenerator vessel 170. The spent catalyst may enter the riser 160 through a catalyst inlet. In one or more embodiments, the riser 160 is in fluid communication with the steam stripping zone 131 of the reactor 100 and the spent catalyst may be passed directly from the steam stripping zone 131 to the riser 160. In one or more embodiments, an air stream 151 is passed to the riser 160, and the air and spent catalyst travel up riser 160. In one or more embodiments, the air stream 151 is used to oxidize at least a portion of the coke on the spent catalyst, restoring activity to the spent catalyst and forming a regenerated catalyst.

The regenerated catalyst and air may move from riser 160 to regenerator vessel 170. In one or more embodiments, the riser 160 and regenerator vessel 170 are adjacent to each other and the regenerated catalyst and air move directly from the riser 160 to the regenerator vessel 170, wherein the riser 160 and regenerator vessel 170 are in direct fluid communication. In one or more embodiments, an air stream 152 may exit the regenerator vessel 170. Additionally, regenerated catalyst may exit the regenerator vessel 170 through a regenerated catalyst outlet. In one or more embodiments, the regenerated catalyst may be included in the catalyst of stream 103. In one or more embodiments, the regenerator vessel 170 and the upper reactor portion 110 may be in fluid communication with each other and regenerated catalyst may be passed directly from the regenerator vessel 170 of the regenerator 150 to the upper reaction zone 111 of the reactor 100 through catalyst inlet 113, wherein the regenerator vessel 170 and the upper reaction zone 111 are in direct fluid communication. In one or more embodiments, fresh catalyst may be added to catalyst in stream 103. In such embodiments, the catalyst may comprise both regenerated catalyst and fresh catalyst.

EXAMPLES

The following examples illustrate one or more additional features of the present disclosure. In the following examples, a hydrocarbon feed stream was cracked to light olefins in the presence of catalyst samples that contained mixtures of spent catalyst and fresh catalyst to simulate a reactor having a lower fluidized bed and an upper counter-current plug flow reaction zone as described in this disclosure.

Example 1: A micro-activity testing (MAT) unit was used to determine the conversion and selectivity of a hydrocarbon stream at different catalyst-to-oil ratios to simulate changing the amount of catalyst (catalyst hold-up) in the counter-current reactor. The hydrocarbon stream was hexane, and cracking occurred at 650° ° C. The catalyst was a ZSM-5 based solid acid catalyst. Catalyst-to-oil ratios of 4.69, 7.06, and 10.61 were examined and the light olefin yields are displayed in Table 1. As displayed in Table 1, the yield of light olefins increased as the catalyst-to-oil ratio increased. Additionally, the yield of coke decreased as the catalyst-to-oil ratio increased. This was likely due to a reduction in the bimolecular reactions that lead to coke formation. Since an increase in catalyst-to-oil ratio correlates to an increased amount of catalyst within the reactor, increasing the catalyst hold-up in the reactor leads to increased hydrocarbon conversion to light olefins. Additionally, the conversion hydrocarbons to light olefins can be achieved in reactors of reduced size when the amount of catalyst in the reactor is increased.

The conversion of hydrocarbons to light olefins using two layers of catalyst was performed in a MAT unit. The hydrocarbon stream was hexane, and cracking occurred at 650° ° C. The first catalyst layer was partially deactivated catalyst. The catalyst was deactivated at 810° C. for six hours under 100% steam. The first catalyst layer made up 30% of the total catalyst in the MAT unit. The first catalyst layer represents the dense fluidized bed portion of the reactor described in the disclosure. The second catalyst layer was fresh catalyst and made up 70% of the catalyst in the MAT unit. The second catalyst layer represents the counter-current plug flow section of the reactor described in the disclosure. The yield of light olefins from hexane cracked by the double layer catalyst is displayed in Table 2. Table 2 also displays the yield of light olefins from the single layer catalyst with a catalyst-to-oil ratio of 10.61 of Example 1. As shown in Table 2, cracking hexane in the presence of the dual layer catalyst resulted in a slight drop in conversion due to the presence of coke on the first catalyst layer. The mol % of $C_2$ to $C_4$ olefins was 45.9 mol % for the dual layer catalyst and 47 mol % for the single layer catalyst. However, when considering the difference in conversion, the dual layer catalyst resulted in a higher selectivity of light olefins over the single layer catalyst. Thus, the dual zone reactor disclosed in the description may provide increased selectivity when used to produce light olefins.

Example 2: A lab scale results from a dense fluidized bed reactor unit, designed to mimic some aspects of the MZFBR claimed in this patent, was used to determine the conversion and selectivity of a hydrocarbon stream at different temperatures. The catalyst was a formulated catalyst having 20 wt. % ZSM-5, 20 wt. % zeolite Y and the remaining are filler, binder and silicon carbide. The estimated WHSV is in excess of 1 $hr^{-1}$. The hydrocarbon feed stream was Arab Light (AL) crude oil, and a co-feed was steam, at an oil:steam ratio of 1:1 by volume (equivalent to an oil:steam ratio of 1:1.16 by mass, or where steam represents 53.7 percent by pass of the total feed). Product yields are presented in Table 3. As shown in Table 3, the light olefins in term of ethylene, propylene and butenes, resulted from the MZFBR bench scale reactor at 625° C. and 650° C. are 38.6 wt. % and 37.5 wt. % respectively. The off-gas and coke yields increase with temperature. It should be mentioned that the amount of coke is increased when crude oil is used without steam. Operating in the absence of steam increased the likelihood of transfer line plugging for example at temperatures above about 500° C. The steam works as a diluent that may prevent a bimolecular reactions and reduce the coke formation.

For the purpose of describing the simplified schematic illustrations and descriptions of FIGS. 1-4, the numerous valves, temperature sensors, electronic controllers and the like that may be employed and well known to those of ordinary skill in the art of certain processing operations are not included. Further, accompanying components that are often included in typical chemical processing operations, such as air supplies, catalyst hoppers, flue gas handling systems, dryers, heaters, heat exchangers, pipes, pumps, compressors, and controllers, are not depicted. Further, while not shown, light gases such as Ct and C; gases from one or more zones can be used a fuel for one or more heaters within the system as is known. Accompanying components that are in cracking units, such as bleed streams, spent catalyst discharge subsystems, and catalyst replacement sub-systems are also not shown. It should be understood that these components are within the spirit and scope of the present embodiments disclosed. It should be understood that the reactor diameter and length or relative diameter and length with respect to the zone should not be inferred from the drawings and that the diameter of the reactor may be similar or different to the depiction in the drawings. Additionally, operational components, such as those described in the present disclosure, may be added to the embodiments described in this disclosure.

It is to be understood that like numerals in the drawings represent like elements through the several figures, and that not all components and/or steps described and illustrated with reference to the figures are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Notably, the figures and examples above are not meant to limit the scope of the present disclosure to a single implementation, as other implementations are possible by way of interchange of some or all the described or illustrated elements. Moreover, where certain elements of the present disclosure can be partially or fully implemented using known components, only those portions of such known components that are necessary for an understanding of the present disclosure are described, and detailed descriptions of other portions of such known components are omitted so as not to obscure the disclosure. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration.

The foregoing description of the specific implementations will so fully reveal the general nature of the disclosure that others can, by applying knowledge within the skill of the relevant art(s), readily modify and/or adapt for various applications such specific implementations, without undue experimentation, without departing from the general concept of the present disclosure. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings accordingly to one example and other dimensions can be used without departing from the disclosure.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

TABLE 1

| Yields | Catalyst-to-Oil Ratio | | |
| | 4.96 | 7.06 | 10.61 |
| | Wt. % | | |
| $H_2$ | 0.226 | 0.293 | 0.358 |
| $C_1$ | 2.34 | 2.88 | 3.23 |
| $C_2$ | 4.94 | 6.28 | 7.40 |
| $C_2=$ | 7.51 | 10.12 | 12.26 |
| $C_3$ | 6.04 | 8.37 | 10.54 |
| $C_3=$ | 16.32 | 19.93 | 22.25 |
| $iC_4$ | 0.23 | 0.38 | 0.53 |
| $nC_4$ | 1.59 | 2.16 | 2.63 |
| $t2C_4=$ | 1.69 | 2.09 | 2.26 |
| $1C_4=$ | 1.57 | 1.82 | 2.02 |
| $iC_4=$ | 2.59 | 3.14 | 3.45 |
| $_c2C_4=$ | 1.39 | 1.70 | 1.87 |
| 1,3-BD | 0.031 | 0.047 | 0.074 |
| $C_4 =$ (liquid) | 0.00 | 0.00 | 0.00 |
| Total Gas | 46.47 | 59.20 | 68.88 |
| Gasoline | 53.30 | 40.70 | 30.96 |
| LCO | 0.00 | 0.00 | 0.00 |
| HCO | 0.00 | 0.00 | 0.00 |

TABLE 2

| Yields | Catalyst Layers | |
| | 1 | 2 |
| | Catalyst-to-Oil Ratio | |
| | 10.61 | 9.60 |
| | Wt. % | |
| $H_2$ | 0.358 | 0.337 |
| $C_1$ | 3.23 | 2.87 |
| $C_2$ | 7.40 | 7.02 |
| $C_2=$ | 12.26 | 11.25 |
| $C_3$ | 10.54 | 10.15 |
| $C_3=$ | 22.25 | 21.27 |
| $iC_4$ | 0.53 | 0.49 |
| $nC_4$ | 2.63 | 2.55 |
| $t2C_4=$ | 2.26 | 2.18 |
| $1C_4=$ | 2.02 | 1.96 |
| $iC_4=$ | 3.45 | 3.33 |
| $_c2C_4=$ | 1.87 | 1.80 |
| 1,3-BD | 0.074 | 0.068 |
| $C_4 =$ (liquid) | 0.00 | 0.00 |
| Total Gas | 68.88 | 65.28 |
| Gasoline | 30.96 | 34.60 |
| LCO | 0.00 | 0.00 |
| HCO | 0.00 | 0.00 |
| Coke | 0.164 | 0.119 |

TABLE 3

| Product Component | Yield (wt. %) at 625 C. | Yield (wt. %) at 650 C. |
| --- | --- | --- |
| Off gas | 6.9 | 9 |
| Propane | 1.9 | 1.6 |
| Ethylene | 10.53 | 11.8 |
| Propylene | 20.5 | 19 |
| Butenes | 7.6 | 6.7 |
| Gasoline | 32.3 | 31.9 |
| Coke | 4.5 | 6 |

The invention claimed is:

1. A method for processing hydrocarbons to produce light olefins, the method comprising:

passing a primary hydrocarbon feed stream, and a co-feed of steam, to a feed inlet of a reactor for contact with catalyst, the co-feed provided in an amount of about 1 to 150 mass percent of the co-feed relative to a mass of the primary hydrocarbon feed stream, wherein the reactor comprises:

an upper reactor portion defining an upper reaction zone, the upper reactor portion comprising a catalyst inlet for receiving the catalyst and a hydrocarbon product outlet, wherein the catalyst inlet and the hydrocarbon product outlet are positioned at or near the top of the upper reaction zone, and wherein a reaction zone refers to an area where a particular reaction takes place in the reactor; and a lower reactor portion defining a lower reaction zone, the lower reactor portion comprising the feed inlet and a catalyst outlet, wherein the feed inlet and the catalyst outlet are positioned at or near the bottom of the lower reaction zone, and wherein the lower reaction zone is in fluid communication with and adjacent to the upper reaction zone; and wherein:

the catalyst has a downward superficial velocity through the upper reaction zone and the lower reaction zone and the hydrocarbon feed stream has an upward superficial velocity through the upper reaction zone and lower reaction zone such that the hydrocarbon feed stream and the catalyst move with a counter-current orientation and contact;

the upper reaction zone operates with a counter-current plug flow regime, wherein a catalyst-to-oil ratio on a mass basis in the upper reaction zone is from about 5 to 100 and the superficial velocity of the hydrocarbon feed stream in the upper reaction zone is about 10 m/s or less;

the lower reaction zone operates with a dense bed fluidization regime, wherein a weight hourly space velocity of the lower reaction zone is from about 1 to 200 hr$^{-1}$; and contacting the catalyst with the hydrocarbon feed stream and the co-feed cracks one or more components of the hydrocarbon feed stream and forms a hydrocarbon product stream, wherein the hydrocarbon product stream comprises light olefins including one or more of ethylene, propylene, or butene, and other reaction products including one or more of dry gas, LPG, aromatics, light naphtha, full range naphtha, heavy naphtha, light cycle oil, or heavy cycle oil; and passing the hydrocarbon product stream out of the upper reaction zone through the hydrocarbon product outlet;

wherein the primary hydrocarbon feed stream comprises one or more of C$_4$ components, light naphtha, heavy naphtha, full range naphtha, vacuum gas oil, crude oil, FCC gasoline, olefinic naphtha, atmospheric residue, vacuum residue, condensate, deasphalted crude oil, dewaxed crude oil, deasphalted-dewaxed crude oil, middle distillates, or kerosene.

2. The method as in claim 1, wherein the co-feed further comprises a recycle stream derived from the hydrocarbon product stream.

3. The method as in claim 1, wherein the co-feed further comprises oxygenates in an amount of about 1 to 50 mass percent of oxygenates relative to a mass of the primary hydrocarbon feed stream.

4. The method as in claim 2, wherein the other reaction products comprise at least light cycle oil, and wherein the co-feed comprises as all or a portion of the recycle stream all or a portion of the light cycle oil, and wherein the recycle stream is provided in an amount of about 1 to 20 mas percent of the co-feed relative to the primary hydrocarbon feed stream.

5. The method as in claim 2, wherein the other reaction products comprise at least light naphtha, and wherein the co-feed comprises as all or a portion of the recycle stream all or a portion of the light naphtha, and wherein the recycle stream is provided in an amount of about 1 to 50 mass percent of the co-feed relative to the primary hydrocarbon feed stream.

6. The method as in claim 3, wherein oxygenates comprises one or more alcohols, ketones or aldehydes.

7. The method as in claim 6, wherein oxygenates comprises methanol.

8. The method as in claim 1, wherein the feed inlet comprises a first feed inlet and a second feed inlet, wherein the first feed inlet is positioned at or near the bottom of the lower reaction zone, wherein the second feed inlet is positioned at or near the middle or top of the lower reaction zone, wherein the primary hydrocarbon feed stream is fed to the first feed inlet, and wherein a secondary hydrocarbon feed stream is fed to the second feed inlet.

9. The method as in claim 1, wherein the primary hydrocarbon feed stream comprises crude oil.

10. The method as in claim 1, further comprising:

passing the catalyst through the catalyst outlet to a catalyst regenerator, wherein the catalyst passing through the catalyst outlet is spent catalyst;

regenerating at least a portion of the spent catalyst to form a regenerated catalyst; and passing the regenerated catalyst to the upper reaction zone through the catalyst inlet.

11. The method as in claim 1, further comprising passing the catalyst through a steam stripping portion of the reactor prior to the catalyst outlet.

* * * * *